United States Patent [19]

Egan et al.

[11] 4,256,611
[45] Mar. 17, 1981

[54] LIGHT DUTY NON-IRRITATING DETERGENT COMPOSITIONS

[75] Inventors: Richard R. Egan, Worthington; Phillip L. Cotrell, Urbana, both of Ohio

[73] Assignee: Sherex Chemical Company, Inc., Dublin, Ohio

[21] Appl. No.: 49,835

[22] Filed: Jun. 18, 1979

Related U.S. Application Data

[63] Continuation of Ser. No. 942,074, Sep. 13, 1978, which is a continuation-in-part of Ser. No. 795,342, May 9, 1977, abandoned.

[51] Int. Cl.³ .................... C11D 1/12; C11D 1/83
[52] U.S. Cl. ..................... 252/548; 252/174.22; 252/550; 252/551; 252/558; 252/559; 252/DIG. 14
[58] Field of Search ................ 252/174.21, 174.22, 252/548, 550, 551, 558, 559, DIG. 1, DIG. 14, 545; 260/410

[56] References Cited

U.S. PATENT DOCUMENTS

| 3,532,636 | 10/1970 | Pacini | 252/558 X |
| 3,538,009 | 11/1970 | Kelly | 252/558 X |
| 3,813,350 | 5/1974 | Kelly | 252/547 |
| 3,944,663 | 3/1976 | Weiss et al. | 424/78 |
| 3,947,384 | 3/1976 | Kelly et al. | 252/542 |

FOREIGN PATENT DOCUMENTS 46-14340 4/1971 Japan.

Primary Examiner—P. E. Willis, Jr.
Attorney, Agent, or Firm—Edward B. Dunning; Burton A. Amernick

[57] ABSTRACT

A liquid detergent system wherein the active content is a combination of an anionic surfactant and a nonionic surfactant in the form of ethoxylated partial glycerol esters of a higher, detergent grade fatty acid and optionally containing a foam stabilizing agent. These systems are particularly useful for formulating shampoos and light duty liquid household cleaning compositions having low eye and skin irritation properties.

9 Claims, 2 Drawing Figures

WEIGHT RATIO OF ETHOXYLATED (30) COCO-MG TO SLES

| BLENDS | PEG 40 GLYCERYL TALLOWATE | PEG 30 GLYCERYL COCOATE |
|---|---|---|
| BLEND 1 | 75% | 25% |
| BLEND 2 | 50% | 50% |
| BLEND 3 | 25% | 75% |

LIGHT DUTY NON-IRRITATING DETERGENT COMPOSITIONS

CROSS-REFERENCE TO RELATED APPLICATION

This is a continuation of application Ser. No. 942,074, filed Sept. 13, 1978, which in turn is a continuation-in-part application of Ser. No. 795,342, filed May 9, 1977, now abandoned.

BACKGROUND OF THE INVENTION

1. Field of the Invention

This invention relates to liquid detergent compositions.

2. Description of the Prior Art

To date, most shampoos and light duty household detergent products have been based on the combination of an anionic surfactant and a surface active agent serving as a foam promoter or stabilizer. Exemplary of the anionics for these applications include sodium lauryl sulfate (SLS), sodium lauryl ether sulfate (SLES) and linear alkyl benzene sulfonate (LAS). Generally, the foam promoter is a tertiary amine oxide or an alkanolamide, either of the so-called superamide or of the Kritchevsky type.

All of the aforementioned surface active agents and particularly the anionics are severe eye irritants and are capable of causing mild to moderate skin irritation to some sensitized persons. Lately, there has been a trend toward substantially ameliorating the irritant effects of such compositions by using the anionic in conjunction with an amphoteric type surfactant and combining these compounds with a nonionic surfactant in the form of an ethoxylate of a partial polyol ester of a higher fatty acid.

The state of the art products of this type, such as the so-called baby shampoo formulations, range in the category of "mildly irritating" in accordance with the Draize eye irritation test. While it would be desirable to provide even blander systems in this respect than are now available, the overriding desiratum, however, is that of obtaining like systems which affords the formulator acceptable latitude in regulating viscosity characteristics of the final products. Most detergent compositions of the type herein concerned are marketed as water solutions containing from about 10 to 30 percent active content. About the only means for regulating viscosity at the indicated range of solids content for the prior art systems necessitates the inclusion of common salt. But this expediency is self-defeating inasmuch as the added salt significantly increases the eye irritation properties of the product.

OBJECT OF THE INVENTION

It is accordingly the object of this invention to provide liquid detergent compositions, particularly shampoos, exhibiting improved eye irritation properties and whose viscosity characteristics can be varied extensively without the inclusion of salt in the formulation for achieving such control.

SUMMARY OF THE INVENTION

In accordance with this invention a low irritation detergent system is provided for formulating household aqueous cleaning compositions which consist essentially of a combination of a nonionic surfactant in the form of an ethylene oxide adduct of partial glycerol esters of a detergent grade fatty acid and an anionic surface active agent selected from the group consisting of a salt of a higher alkyl sulfate or sulfonate, a salt of a higher alkyl ether sulfate and a salt of a higher alkyl benzene sulfonate, and which combination optionally include a foam stabilizing amount of an alkanolamide or a tertiary amine oxide. The relative proportion the nonionic surfactant bears weightwise to the anionic surfactant represents the factor in controlling the irritation level of the system.

An important aspect of the present invention beyond that of providing detergent systems having minimal eye irritation properties resides in the ability to vary extensively the viscosity of dilute aqueous solutions thereof through the appropriate choice of the nonionic surfactant component.

DESCRIPTION OF THE PREFERRED EMBODIMENT

Figure 1:
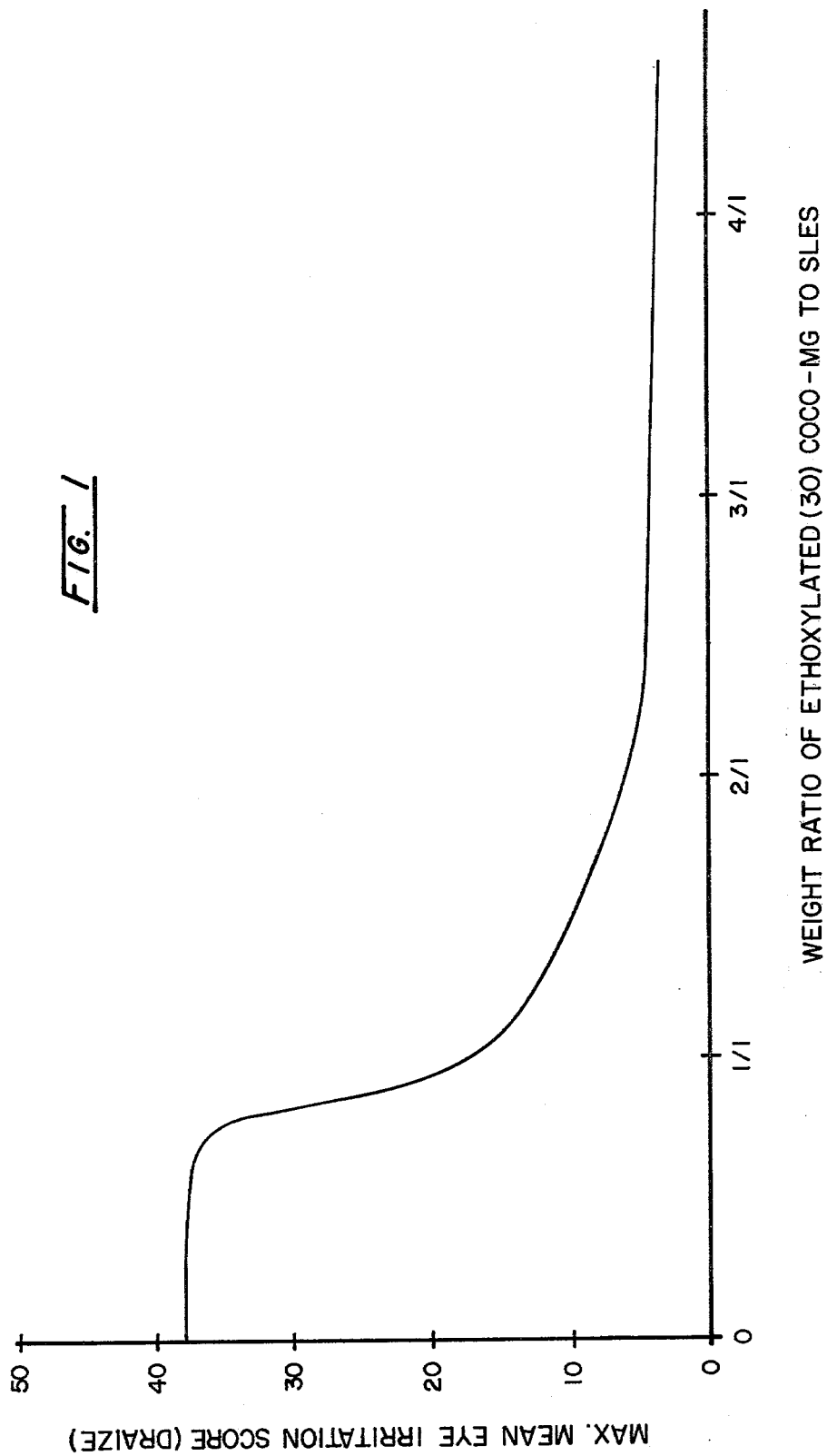
FIG. 1 graphically illustrates the reduction of eye irritant levels as determined in accordance with the Draize eye irritation test resulting from combining the anionic surfactant SLES with varying amounts of a representative nonionic surfactant.

The anionic surfactants useful in the practice of this invention are standard items of commerce and hence need not be further elaborated upon herein. Applicable salts thereof are those of an alkali metal hydroxide, preferably sodium hydroxide, ammonium hydroxide, a hydroxy alkyl amine, etc. The contemplated nonionic surfactants although likewise commercially available, nevertheless warrant a brief description as to how they can be made. As will be brought out later, there may be a need for tailormaking these products so as best to meet the particular requirements of the detergent formulator from the standpoint of viscosity control.

The nonionic surfactants are derived from partial glycerol esters of a higher fatty acid. The applicable higher fatty acids are the saturated or unsaturated, preferably the saturated type, of the so-called detergent grade acids having a carbon atom content of from about 10 to 18. Such partial esters consist essentially of a mixture of monoglycerides and diglycerides. The broadly applicable partial esters of this type have a monoglyceride content of from about 15 to 45 wt. %. More preferably, the monoglyceride content $(\alpha+\beta)$ ranges from about 25 to 35 wt. %. As indicated, the balance of the partial ester product will be predominantly the corresponding diglyceride.

These mono- and diglyceride mixtures can be readily prepared by the glycerolysis of a triglyceride in the presence of a basic catalyst, preferably an alkali metal hydroxide. Alternatively, they can be prepared by directly esterifying glycerin with the fatty acids. The molar ratio of triglyceride to glycerin can be adjusted in carrying out the preferred glycerolysis method to result in a reaction product having a monoglyceride content hereinabove specified. In accordance with this procedure, a mole of the triglyceride is transesterified with slightly in excess of one mole of glycerin to yield a product having the preferred monoglyceride content.

The nonionic surfactants useful herein are the ethylene oxide adducts of the partial glycerol esters described above. In preparing these adducts, from about 15 to 100 moles of ethylene oxide are reacted per mole of the partial ester mixture to provide, in the main, the following idealized structures where n represents the number of moles of ethylene oxide utilized in the reaction.

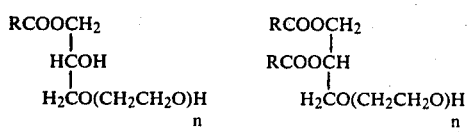

The condensation of the partial glycerol ester with the ethylene oxide can be accomplished under reaction conditions heretofore observed in carrying out the adduction reaction. Thus, ethylene oxide and the partial ester product can be condensed by heating these reactants together in the presence of a suitable catalyst; e.g., an alkali metal hydroxide, at a temperature from about 300°–350° F. and at a pressure from about 20-150 psig.

The nonionic surfactant is combined with that amount of the anionic surfactant which provides an overall composition denoted as "minimally irritating" to the eye in accordance with the Draize test. The general method for evaluating and scoring in accordance with this test is outlined in the J. Pharmacol. and Exp. Ther. 82, page 377 (1944) as well as in Section 191.12 of Federal Hazardous Substance Act. The ratio of nonionic to the anionic for achieving the indicated level of irritation is at least one part by weight of the nonionic surfactant to one part of the anionic surfactant. This minimum ratio is applicable only for those compositions devoid of a foam stabilizer in either the form of an amine oxide of an alkanolamide. The applicable maximum ratio of nonionic to anionic is an aspect turning mainly on overall detergency and/or viscosity considerations and in that light is about 4:1, respectively.

In connection with the foregoing, reference is now had to FIG. 1 wherein a plot is given for the eye irritation levels exhibited by various combinations of a representative nonionic surfactant and SLES. Maximum mean eye irritation scores from 1 to about 18 are classified as being "minimally" irritating. Thus it can be seen that where the nonionic and anionic surfactants are combined on about an equal basis, this low level of irritation is realized. As further shown in the graph, the effect of increasing the proportion of the nonionic surfactant to anionic surfactant is such that an irritation value substantially less than 10 is asymptotically reached at about a ratio of 2:1, respectively. While only a minimal change in eye irritation value occurs beyond this ratio, there still may be a need or an advantage attendant to the use of higher ratios of the nonionic to anionic surfactant from the standpoint of viscosity control, all as will be subsequently explained.

The inclusion of a foam stabilizer of the types applicable for this purpose, notably the superamides, has the effect of increasing the eye irritation characteristics of the system beyond that normally to be expected. However, this increase can be compensated for by moderately increasing the minimum ratio of nonionic to anionic surfactant. Generally, the amount of foam stabilizer is based upon the amount of the anionic surfactant component present in the system, such being from about 20 to 25% of the anionic surfactant component. Amounts of the foam stabilizer less than the specified lower limit results in less than optimum foam stabilization properties. On the other hand, amounts of the stabilizer in excess of the higher limit specified is normally to be avoided because of the rinsing problems caused by the presence of such excessive amounts of the stabilizer. Thus, within the indicated range of stabilizer content, a minimum ratio of two parts by weight of the nonionic to one part by weight of the anionic surfactant will provide an overall composition having a mean eye irritation score in the "minimally" category. Data supporting the foregoing are given in the working example presented herein.

Figure 2:
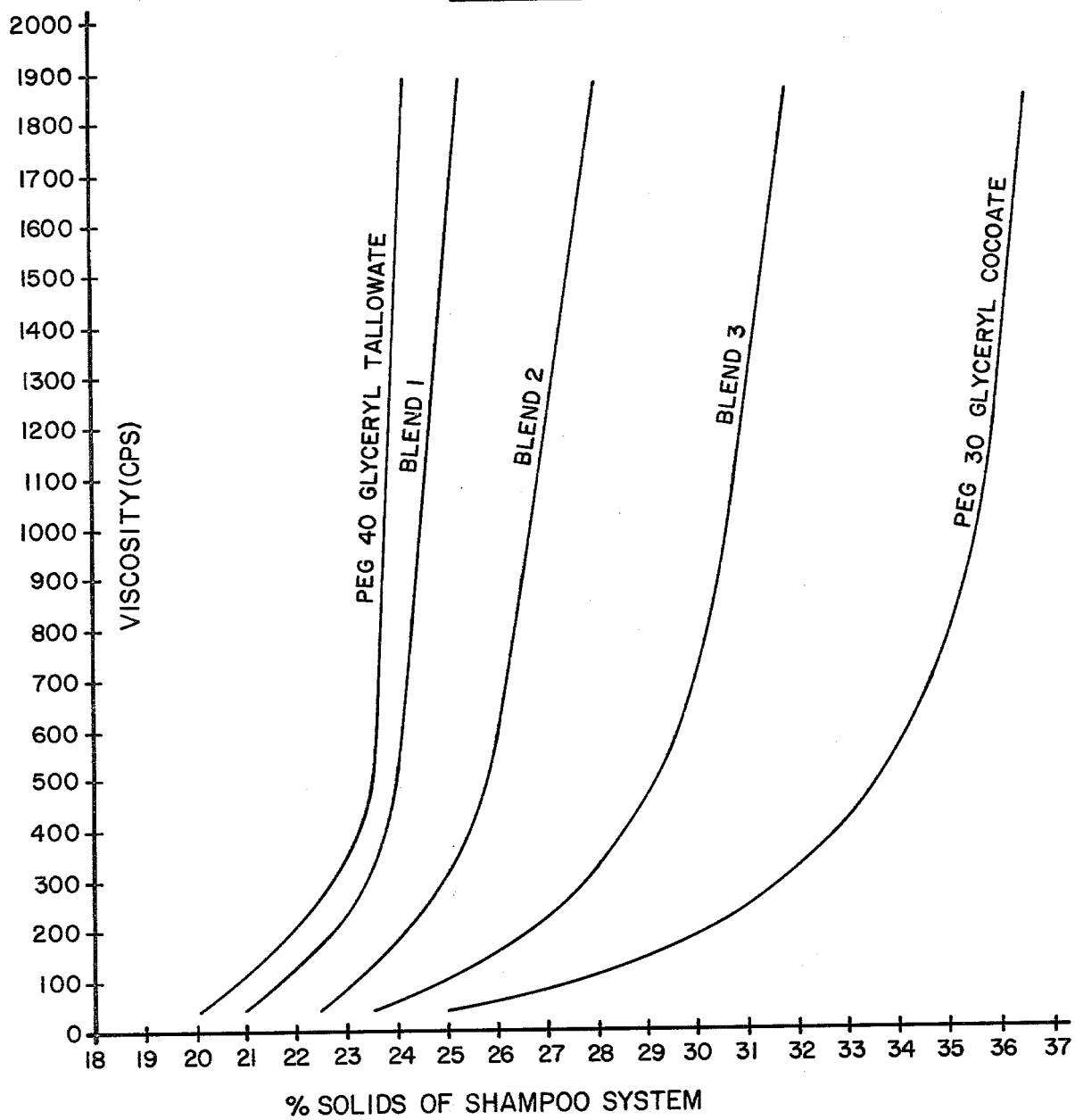
FIG. 2 graphically illustrates the manner whereby the viscosity of a typical shampoo formulation at a conventional range of solids content can be varied by appropriately altering the hydrophobicity characteristics of the nonionic surfactant component.

As mentioned above, an important feature of the present invention resides in the ability to regulate the viscosity of aqueous solutions of the contemplated detergent systems by appropriate selection of the nonionic surfactant component. This feature is illustrated in FIG. 2. In this graphical representation, viscosity is plotted against percent solids of a typical aqueous shampoo system. The active content of the system used for this illustration corresponds to formulation No. 8 of Example I and as such includes, on a solid weight basis, 23.9% of SLES, 71.4% of the nonionic surfactant and 4.6% of a commercial superamide. Basically, two types of nonionic surfactants were used in obtaining the plot data shown in FIG. 2. The preparation of these ethoxylates is likewise given in the example.

As can be noted from FIG. 2, the viscosity of the aqueous system is dependent upon the nature of the nonionic surfactant and the percent of total solids in the system. As shown, the greatest buildup of viscosity can be achieved by using a 40 mole adduct of a mixture of mono- and diglycerides derived from tallow. On the other hand, substituting a 30 mole adduct of a comparable partial ester mixture of coconut fatty acids therefor permits higher solids levels in obtaining the corresponding viscosity associated with the use of the tallowate adduct. Further, it can be seen that complete control of viscosity characteristics can be achieved within the normal range of solids concentration of the detergent system by judiously blending these two representative partial glycerol adducts. It is important to note that FIG. 2 is given for illustrative purposes only and not necessarily meant to limit the invention to the use of the two types of nonionic surfactants represented therein.

The following working example supplements the foregoing in providing a description of the best mode contemplated for carrying out the present invention. While forming no part of this invention, the example further illustrates the manner in which representative nonionic surfactants useful in the practice of the invention can be prepared; namely, the types referred to in FIGS. 1 and 2. The principal purpose of this exemplification, however, is to show how the relationship of the nonionic surfactant component to the anionic can be varied to compensate for eye irritation properties arising from the inclusion in the detergent system of various amounts of a typical alkanolamide foam stabilizing agent. Consistent with the disclosure heretofore given, all parts and percentages specified are by weight.

EXAMPLE I

PEG 30 Glycerol Cocoate

Into a suitable reaction vessel were charged 2335 parts (3.57 moles) refined coconut oil, 345 parts (3.75 moles) glycerin, and 5.4 parts of 50% aqueous KOH.

With stirring, the reaction mixture was heated to 110° C. and held for one hour under 20 mm vacuum. The reaction mixture was then heated to 165° C. with a nitrogen sparge and held for 3 hours.

To a pressure vessel was charged 254.5 parts (0.6 mole) of the above mono- and diglyceride mixture. The reactor was purged twice with nitrogen and heated to 150° C. Ethylene oxide in the amount of 800 parts (18.2 moles) was added over an 8-hour period while maintaining the temperature at 150°–160° C. Upon cooling the reaction mixture to about 110° C., 25% aqueous sulfuric acid was added for neutralization (pH 8) and the reaction mixture then filtered.

PEG 40 Glycerol Tallowate

In a manner described above one mole of tallow was reacted with 1.05 mole of glycerin in the presence of potassium hydroxide to provide a mixture of tallow mono- and diglycerides. Following stripping to remove moisture, the partial ester mixture was then reacted with 40 moles of ethylene oxide as per the procedure outlined above whereupon the ethoxylated product was cooled, stripped and filtered.

In the following Table I, the irritation data given refer to that derived in accordance with the Draize test method. The foam stabilizer indicated is a coco superamide (VARAMIDE MA1-ASHLAND CHEM. CO.). The percentages of the active components are above set forth with the balance being water.

TABLE I

| | SHAMPOO FORMULATIONS | | | | | |
|---|---|---|---|---|---|---|
| | WT. % OF ACTIVE COMPONENTS | | | | | |
| No. | SLES[2] | PEG 30 GLYC.COCOATE[1] | COCO SUPERAMIDE | MEAN IRR SCORE | IRR CLASS. | RATIO (1)/(2) |
| 1 | 4.8 | 22.0 | 1.2 | 10.0 | Minimally | 4.6/1 |
| 2 | 8.0 | 18.0 | 2.0 | 19.7 | Mildly | 2.3/1 |
| 3 | 6.4 | 20.0 | 1.6 | 6.4 | Minimally | 3.1/1 |
| 4 | 5.6 | 21.0 | 1.4 | 6.0 | Minimally | 3.8/1 |
| 5 | 7.2 | 19.0 | 1.8 | 9.3 | Minimally | 2.6/1 |
| 6 | 5.0 | 22.0 | 1.0 | 4.0 | Minimally | 4.4/1 |
| 7 | 8.3 | 18.0 | 1.7 | 5.3 | Minimally | 2.2/1 |
| 8 | 6.7 | 20.0 | 1.3 | 3.3 | Minimally | 3.0/1 |
| 9 | 5.8 | 21.0 | 1.2 | 5.0 | Minimally | 3.6/1 |
| 10 | 7.5 | 19.0 | 1.5 | 5.3 | Minimally | 2.5/1 |

What is claimed is:

1. A low eye and skin irritant detergent composition comprising:
   (a) an ethylene oxide adduct of a partial glycerol ester of a $C_{10}$–$C_{18}$ fatty acid having a monoglyceride content of from about 15 to 45 wt. % with diglycerides essentially constituting the balance, said adduct prepared by reacting one mole of the partial glycerol ester per about 15 to 100 moles of ethylene oxide;
   (b) anionic surface-active agent selected from the group of salt of higher alkyl sulfate or salt of higher alkyl ether sulfate or salt of higher alkyl benzene sulfonate; and
   wherein the weight ratio of (a) to (b) is between about 1:1 and 4:1, respectively.

2. A low eye and skin irritant detergent composition comprising:
   (a) an ethylene oxide adduct of a partial glycerol ester of a $C_{10}$–$C_{18}$ fatty acid having a monoglyceride content of from about 15 to 45 wt. % with diglycerides essentially constituting the balance, said adduct prepared by reacting one mole of the partial glycerol ester per about 15 to 100 moles of ethylene oxide:
   (b) anionic surface-active agent selected from the group of salt of higher alkyl sulfate or salt of higher alkyl ether sulfate or salt of higher alkyl benzene sulfonate; and
   (c) an alkanolamide foam stabilizing agent;
   wherein the weight ratio of (b) to (c) is about 4:1 to 5:1, respectively, and wherein the weight ratio of (a) to (b) is about 2:1 to 5:1, respectively.

3. The detergent composition of claim 1 or 2 wherein said anionic surface-active agent is sodium lauryl sulfate, sodium lauryl ether sulfate, or sodium $C_{12}$–$C_{18}$ alkyl benzene sulfonate.

4. The composition of claim 1 or 2 wherein said partial glycerol ester has a monoglyceride content of about 25 to 35 wt. %.

5. The composition of claim 1 or 2 wherein said adduct is prepared by reacting about one mole of a partial glycerol ester of coconut oil per about 30 moles of ethylene oxide.

6. The composition of claim 1 or 2 wherein said adduct is prepared by reating about one mole of a partial ester of tallow per about 40 moles of ethylene oxide.

7. The composition of claim 1 or 2 being in the form of a dilute aqueous preparation.

8. The composition of claim 1 or 2 wherein said partial glycerol ester is from tallow.

9. The composition of claim 1 or 2 wherein said partial glycerol ester is from coconut oil.

* * * * *